(12) United States Patent
Lei et al.

(10) Patent No.: US 12,280,217 B2
(45) Date of Patent: Apr. 22, 2025

(54) HEATER PLATE

(71) Applicants: VINCENT MEDICAL (DONG GUAN) MANUFACTURING CO., LTD., Guangdong (CN); VINCENT MEDICAL (DONGGUAN) TECHNOLOGY CO., LTD., Guangdong (CN)

(72) Inventors: Yu Lei, Guangdong (CN); Jiebing Xu, Guangdong (CN); Haibin Yu, Guangdong (CN); Zhenxiang Hu, Guangdong (CN); Jun Zhao, Guangdong (CN)

(73) Assignees: VINCENT MEDICAL (DONG GUAN) MANUFACTURING CO., LTD., Guangdong (CN); VINCENT MEDICAL (DONGGUAN) TECHNOLOGY CO., LTD., Guangdong (CN)

( * ) Notice: Subject to any disclaimer, the term of this patent is extended or adjusted under 35 U.S.C. 154(b) by 841 days.

(21) Appl. No.: 17/437,508

(22) PCT Filed: Jun. 6, 2019

(86) PCT No.: PCT/CN2019/090386
§ 371 (c)(1),
(2) Date: Sep. 9, 2021

(87) PCT Pub. No.: WO2020/243955
PCT Pub. Date: Dec. 10, 2020

(65) Prior Publication Data
US 2022/0152337 A1  May 19, 2022

(51) Int. Cl.
*A61M 16/16* (2006.01)
*F24H 9/20* (2022.01)
(Continued)

(52) U.S. Cl.
CPC .......... *A61M 16/16* (2013.01); *F24H 9/2014* (2013.01); *F24H 15/132* (2022.01); *F24H 15/25* (2022.01);
(Continued)

(58) Field of Classification Search
CPC ............ A61M 16/16; F24H 15/10–132; F24H 15/174–175; F24H 15/20–225
See application file for complete search history.

(56) References Cited

U.S. PATENT DOCUMENTS

| | | | |
|---|---|---|---|
| 10,252,019 B2 * | 4/2019 | Potharaju | .............. A61M 16/16 |
| 2003/0164366 A1 | 9/2003 | Baum et al. | |

(Continued)

FOREIGN PATENT DOCUMENTS

| | | |
|---|---|---|
| CN | 103747828 | 4/2014 |
| CN | 107829125 | 3/2018 |

(Continued)

OTHER PUBLICATIONS

International Search Report issued in PCT/CN2019/090386 dated Mar. 10, 2020.

(Continued)

*Primary Examiner* — Joseph D. Boecker
*Assistant Examiner* — Thomas W Greig
(74) *Attorney, Agent, or Firm* — Workman Nydegger

(57) ABSTRACT

A heat plate for a humidifier contains a thermally conductive plate having a top surface and a bottom surface opposite the top surface. A temperature sensor is affixed to the bottom surface and a thermally conductive layer is directly-affixed (Continued)

to the bottom surface. A ceramic heating element is directly affixed to the thermally conductive layer. A humidifier and medical device may also contain such a heater plate.

18 Claims, 3 Drawing Sheets

(51) Int. Cl.
   *F24H 15/132* (2022.01)
   *F24H 15/25* (2022.01)
(52) U.S. Cl.
   CPC ............... *A61M 2205/3368* (2013.01); *A61M 2205/3646* (2013.01)

(56) References Cited

U.S. PATENT DOCUMENTS

| | | | |
|---|---|---|---|
| 2006/0037613 A1* | 2/2006 | Kwok | A61M 16/16 128/203.26 |
| 2006/0055069 A1* | 3/2006 | DiMatteo | A61M 16/16 261/DIG. 65 |
| 2007/0125376 A1* | 6/2007 | Reinstadtler | A61M 16/1075 128/203.26 |
| 2008/0302361 A1* | 12/2008 | Snow | A61M 16/109 128/202.27 |
| 2009/0000620 A1* | 1/2009 | Virr | A61M 16/16 261/150 |
| 2009/0095819 A1 | 4/2009 | Brown et al. | |
| 2009/0107980 A1* | 4/2009 | Andel | A61M 16/109 219/443.1 |
| 2009/0229606 A1 | 9/2009 | Tang et al. | |
| 2009/0320840 A1* | 12/2009 | Klasek | A61M 16/1095 128/203.26 |
| 2014/0131904 A1* | 5/2014 | Tang | A61M 16/16 261/157 |
| 2014/0216459 A1* | 8/2014 | Vos | A61M 16/16 128/204.17 |
| 2015/0115483 A1* | 4/2015 | Miller | A61M 16/024 261/142 |
| 2016/0256659 A1* | 9/2016 | Poormand | A61M 16/0488 |

FOREIGN PATENT DOCUMENTS

| | | |
|---|---|---|
| DE | 29702813 U1 | 5/1997 |
| EP | 101772985 | 7/2010 |
| EP | 3345646 | 7/2018 |
| EP | 3345646 A1 | 7/2018 |
| JP | S63101490 | 7/1988 |
| JP | 07293914 | 11/1995 |
| JP | 11279406 | 10/1999 |
| JP | 2011190311 | 9/2011 |
| JP | 2013020854 | 1/2013 |
| JP | 2014519916 | 8/2014 |
| JP | 2015219498 | 12/2015 |
| JP | 2018070800 | 5/2018 |
| WO | 2008150171 A1 | 12/2008 |
| WO | 2012077052 A1 | 6/2012 |

OTHER PUBLICATIONS

European Extended Search Report for European Application No. 19931775.1, dated Dec. 15, 2022, 8 pages.
Japanese Notice of Reasons for Refusal for Japanese Application No. 2021-563627, dated Nov. 24, 2022, 12 pages with English translation.
Japanese Notice of Reasons for Refusal for Japanese Application No. 2021-563627, dated May 24, 2023, 12 pages with English translation.

* cited by examiner

HEATER PLATE

CROSS-REFERENCE TO RELATED APPLICATION

This application is a national stage application filed under 37 U.S.C. 371 based on International Patent Application No. PCT/CN2019/090386, filed Jun. 6, 2019, which is incorporated herein by reference in its entirety.

FIELD OF THE INVENTION

The present invention relates to heater plates and more particularly to heater plates useful to provide humidified air or humidified gas.

BACKGROUND

Humidifiers are common appliances and devices for providing humidified air or humidified gas. Humidifiers are used in houses, hospitals, etc. and come in a variety of forms. Humidifiers may employ either heat or ultrasonic vibrations. Humidifiers and other medical devices therefore often contain a heater plate which heats up to conduct thermal energy to, for example, water, or a container containing water, so as to cause the water to evaporate and/or even boil. Typical heater plates contain a heating element, usually an electrical heating element, recently, ceramic heating elements have become popular and are used in, for example, respiratory humidifiers, to assist with patients who require breathing humidified air. See, for example, U.S. Pat. No. 9,821,135 B2 to Tang, et al., granted on Nov. 21, 2017 and assigned to ResMed Ltd.

Heaters, humidifiers and medical devices often contain a variety of sensors to detect, for example, the heater plate temperature, the water level in a water reservoir, the presence or absence of a water reservoir, the humidity of the air, etc. In many instances, the temperature of the heater plate is measure via indirect contact or by calculating the temperature. However, it has now been found that such methods may be inaccurate, with temperature variances of up to, for example, 10° C.

This temperature variance can in turn lead to insufficient humidity in the gas, or too much humidity in the gas. This may also lead to the gas being too hot or too cold for the patient. This could also lead to other problems, such as bacterial growth in the water reservoir, and/or the water reservoir going dry as all the water is evaporated therefrom.

Accordingly, it is desirable to more accurately measure the heater plate temperature.

SUMMARY OF THE INVENTION

In an embodiment herein, a heater plate for a humidifier contains a thermally-conductive plate having a top surface and a bottom surface opposite the top surface. A temperature sensor is affixed to the bottom surface and a thermally-conductive layer is directly-affixed to the bottom surface. A ceramic heating element is directly-affixed to the thermally-conductive layer.

Without intending to be limited by theory, it is believed that the inventors found that previous techniques to indirectly measure or estimate the temperature of the heater plate were inaccurate, and could vary by, for example, 10° C. This in turn could lead to excessive energy usage, humidified air which is too hot for a patient, humidified air which is too cold for a patient, humidified air which does not carry enough moisture and therefore is too dry for the patient, humidified air which carries too much moisture, leading to increased condensation in the breathing circuit, and/or which varies greatly in temperature from one minute to the next. In contrast, by affixing a temperature sensor directly to the bottom surface of a heater plate's thermally-conductive plate, and even better, between multiple ceramic heating elements, it is believed that the present invention may more accurately measures the real temperature of the heater plate, instead of estimating it. This in turn may provide more accurate and immediate feedback by the device's controller/microprocessor. Furthermore, it is believed that the present invention may provide a heater plate with a more evenly-distributed heating profile.

Figure 1:
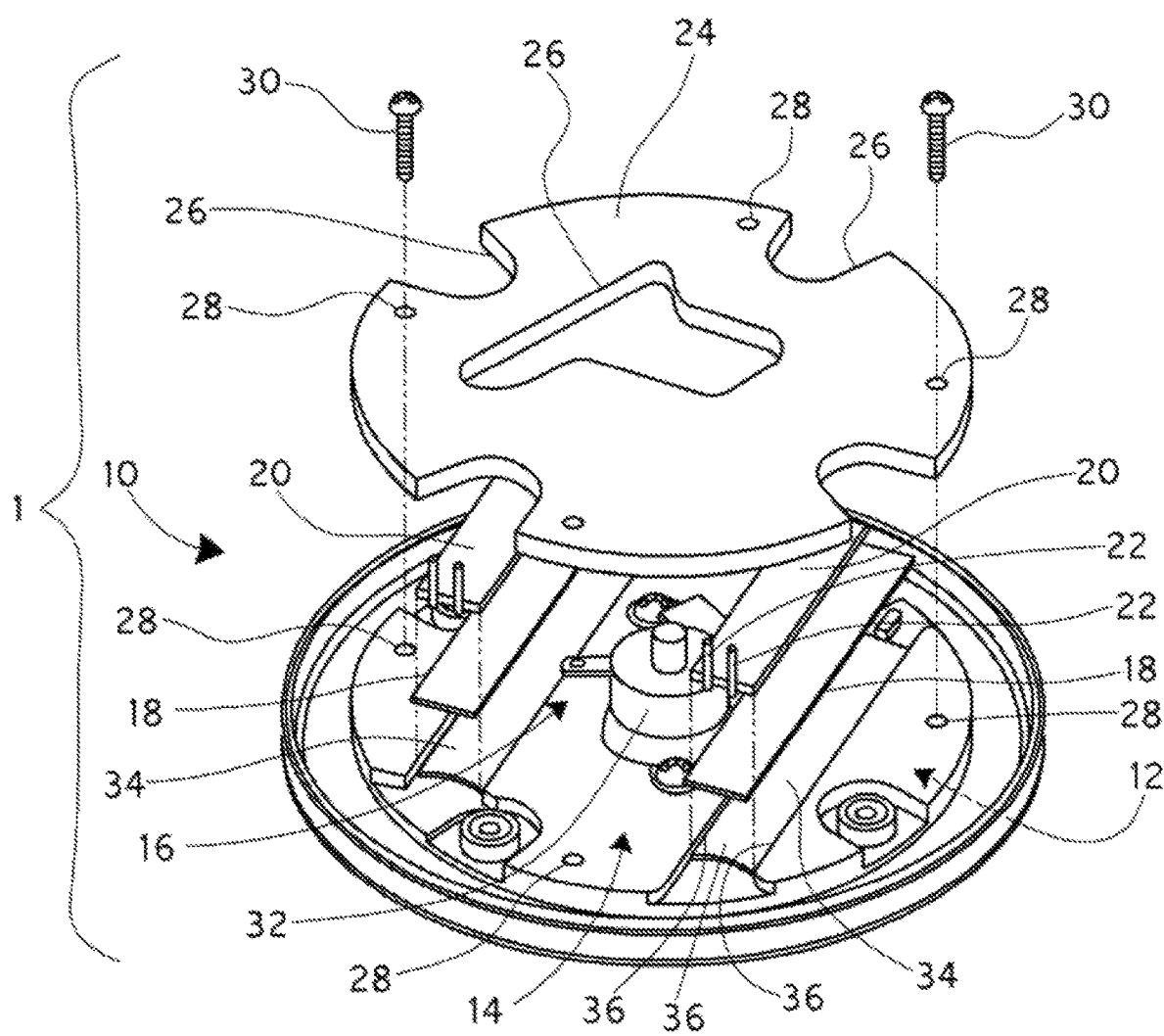
FIG. 1 shows an upside-down, exploded view of an embodiment of a heater plate of the present invention.

The figures herein are for illustrative purposes only and are not necessarily drawn to scale.

DESCRIPTION OF THE PREFERRED EMBODIMENTS

Unless otherwise specifically provided, all measurements are made in metric units. Furthermore, all percentages, ratios, etc. herein are by weight, unless specifically indicated otherwise.

As used herein, the term "affixed to" and variations thereof indicate that two or more items are connected to each other, either directly or indirectly, as desired. Thus, in the absence of other descriptors, the term "affixed to" and variations thereof includes both "directly affixed to" and "indirectly affixed to".

An embodiment of the present invention relates to a heater plate containing a thermally-conductive plate containing a top surface and a bottom surface. The bottom surface is opposite the top surface and contains a temperature sensor affixed to the bottom surface, a thermally-conductive layer directly affixed to the bottom surface, and a ceramic heating element directly affixed to the thermally-conductive layer.

The heater plate may be used to heat up, for example, water in a water reservoir for a humidifier/humidification system, or a medical device. Humidifier and humidification systems, as well as medical devices employing heater plates are well-known in the art.

In order to accurately determine the temperature of the heater plate, a temperature sensor is affixed to the bottom surface of the thermally-conductive plate which forms part of the heater plate. The temperature sensor may be affixed either directly or indirectly to the bottom surface of the thermally-conductive plate. In an embodiment herein the temperature sensor is directly affixed to the bottom surface of the thermally-conductive plate. Without intending to be limited by theory it is believed that affixing the temperature sensor to; or directly to, the bottom surface allows a better direct measurement of the temperature, rather than via indirectly measuring and/or estimating the temperature. In an embodiment herein, the temperature sensor is located near the ceramic heating element; or, if there are a plurality of ceramic heating elements, then the temperature sensor may be located between at least two ceramic heating elements; or between a plurality of ceramic heating elements.

The temperature sensor may generally be any type known in the art. In an embodiment herein, the temperature sensor herein is selected from a negative temperature coefficient (NTC) sensor, a positive temperature coefficient (PTC) sensor, a platinum resistance temperature sensor, a digital temperature sensor, and a combination thereof; or a NTC sensor. In an embodiment herein, the temperature sensor is a band gap temperature sensor on an integrated circuit, such as the Sensirion humidity and temperature sensor, SHT21, available from https://www.sensirion.com/en/. It is believed that such temperature sensors provide good stability, and high precision over the desired temperature range.

The thermally-conductive layer enhances heat transfer between the ceramic heating element and the bottom surface of the thermally-conductive plate. Typically a ceramic heating element is hard but brittle and therefore it is inadvisable to make the heater plate and/or the thermally-conductive plate itself of a ceramic material. However, by placing a thermally-conductive layer between the bottom surface and the ceramic heating element, the contact between these pieces is made more complete and also heat transfer is enhanced, while the heater plate and/or the thermally-conductive plate protects the ceramic heater element(s) from impacts, moisture, etc. In an embodiment herein the thermally-conductive layer is an adhesive layer which helps to seal and ensure that the ceramic heating element is firmly affixed to the bottom surface. In an embodiment herein, the thermally-conductive layer contains a thermally-conductive silicone sheet, a thermally-conductive adhesive, a thermally-conductive silicone grease, and a combination thereof; or a thermally-conductive silicone sheet, a thermally-conductive adhesive, and a combination thereof; or a thermally-conductive silicone sheet and a thermally-conductive adhesive. Without intending to be limited by theory it is believed that a thermally-conductive silicone sheet may provide a shock absorptive effect, thereby protecting the heating element, especially a ceramic heating element which may be brittle. Without intending to be limited by theory it is believed that s thermally-conductive silicone grease may provide improved heat transfer without tending to become hard and brittle over time.

Ceramic heating elements are known in the art (see, U.S. Pat. No. 4,939,349 to Liu, granted on Jul. 3, 1990 assigned to Uppermost Electronic Industries, Co., Kaohsiung, Taiwan), and may be formed in a variety of shapes and sizes. Such ceramic heating elements are available from multiple manufacturers worldwide and available in, for example, the form of strips or plates; or strips; or long strips in a range of properties. In an embodiment herein, the ceramic heating element is effective at a wattage range from about 100 W to about 250 W. Without intending to be limited by theory, it is believed that ceramic heating elements provide one or more benefits such as high thermal conductivity, a small size, efficient heat generation, and/or a long life.

However, as noted, ceramic heating elements may be brittle and have a low impact resistance. Accordingly, they are typically not intended to form the top surface of the heater plate and/or the thermally-conductive plate which needs to be resistant to impacts, dropping, etc. As such, the ceramic heating element will typically cover only a portion of the bottom surface, thereby also allowing the attachment of other items, such as, for example, the temperature sensor to the bottom surface. In a preferred embodiment herein, the ceramic heating element contains a plurality of ceramic heating elements, affixed directly, or indirectly, to the bottom surface of the thermally-conductive plate. In an embodiment herein, the ceramic heating element is evenly-arranged at intervals around the bottom surface; or in a ring; or a plurality of concentric rings.

In an embodiment herein, the heater plate contains a plurality of ceramic heating elements; or from about 2 to about 10 ceramic heating elements; or from about 2 to about 6 ceramic heating elements; or from about 2 to about 4 ceramic heating elements; or about 2 ceramic heating elements. In an embodiment herein, the ceramic heating element is in the form of a strip; or a thin strip; or a plurality of strips; or a plurality of thin strips. In an embodiment herein, the strip has at least 1 face; or from about 1 face to about 6 faces. Typically each face will be flat, but it is recognized that each face may be a different shape, and/or that a face may be curved. Without intending to be limited by theory, it is believed that multiple heating elements evenly-distributed around the bottom surface may provide a more even heat distribution across the heater plate, so that the thermally-conductive plate will have a more evenly-distributed heating profile, which in turn leads to more even evaporation of the water. Without intending to be limited by theory, it is believed that an additional benefit of a ceramic heating element in the form of a strip, or a thin strip, is that the ceramic heating element is less likely to crack or break over time; or over long heating times, due to the relatively small area and thin profile. In an embodiment herein, the temperature sensor is positioned between the plurality of ceramic heating elements, and the temperature sensor and the ceramic heating elements are affixed to the thermally-conductive plate. Therefore, the temperature sensor directly detects the temperature of the thermally-conductive plate.

When employing a heater plate to heat up, for example, water in a water reservoir, it is often important to be able to tell whether or not the water reservoir is even present. Accordingly, in an embodiment herein, a water reservoir sensor is included herein to detect the presence or absence of a water reservoir, and/or to detect whether the water reservoir is present, correctly placed and/or correctly attached. If the water reservoir is not present, not correctly placed and/or not correctly attached, then the water reservoir sensor may directly or indirectly prevent the heater plate from activating by, for example, breaking the heater plate's heating element circuit, either physically or electrically.

In addition, to prevent the heater plate from being activated when the water has all evaporated, it may also be desirable to be able to tell whether or not there is sufficient water in the water reservoir. Accordingly, in an embodiment herein, the heater plate further contains a water level sensor; or a pressure-sensitive water level sensor, an optical water-level sensor, a water-level temperature sensor, and a combination thereof; or an optical water level sensor. A pressure-sensitive water level sensor may be positioned below the bottom of the heater plate. The pressure-sensitive water level sensor may or may not be in physical contact with the heater plate when no water reservoir is placed on the heater plate and/or when insufficient water is placed in the water reservoir, as desired. When a water reservoir of a minimum weight (i.e., including a minimum amount of water) is placed on the heater plate, then the heater plate may descend or drop down so as to physically activate the switch. In an embodiment herein, the switch contains a spring or other device which biases the switch to a specific position and/or which prevents activation of the switch unless a predetermined weight (i.e., the water reservoir and the water therein) pressed down upon the heater plate.

Alternatively, an optical water level sensor may detect when sufficient water is present, so as to allow the heater plate's heating element circuit, to activate. In another embodiment, a water-level temperature sensor may detect if the temperature of the heater plate and/or the water reservoir is above a predetermined temperature, such as, for example, 100° C.; or 101° C.; or 105° C., which would indicate that insufficient water is present in the water reservoir.

In an embodiment, when device is satisfied that the water reservoir is present and that sufficient water is provided therein, then the heater plate's heating element circuit is closed and the circuit is completed so that electricity may flow into the heating element. However, when the device is not satisfied that the water reservoir is present and that sufficient water is provided therein, then the heater plate's heating circuit is an open circuit, and therefore electricity is stopped and may not flow through the heating element.

In an embodiment herein to prevent the dislodging of the temperature sensor, the thermally-conductive layer, and/or the ceramic heating element(s) herein from the heater plate, a protective plate may be provided. In an embodiment herein the protective plate is affixed to the bottom surface and therefore sandwiches the thermally-conductive layer, and/or the ceramic heating element between the bottom surface and the protective plate. Thus, the thermally-conductive layer, and/or the ceramic heating element are located between the bottom surface and the protective plate. Without intending to be limited by theory, it is believed that the protective plate may also reflect heat from the ceramic heating element(s) back towards the heater plate, thereby increasing the thermal efficiency of the heater plate. Without intending to be limited by theory it is also believed that the thermally-conductive layer may also reduce the chance of a spark being generated from a short-circuit between the ceramic heating element and the bottom surface of the heater plate. As such a heater plate, humidifier, medical device, etc. may be used in a hospital or other environment where a patient may need a higher-than-normal oxygen content, it is especially important to avoid sparks and short-circuits.

In an embodiment herein, the thermally-conductive plate, the protective plate, or both may contain a metal; or aluminium; or steel; or a combination of aluminium and steel, as it is believed that metal; or aluminium, or steel, conduct heat efficiently, are easy to form into the desired shapes, and/or a combination thereof. In an embodiment herein, the thermally-conductive plate is formed of an aluminium alloy, such as aluminium alloy AA6061, and aluminium alloy AA6063, as defined by the Aluminium Association of Arlington Virginia, USA, both of which are available from multiple suppliers worldwide. Without intending to be limited by theory, it is believed that an aluminium alloy. may improve overall heat conduction efficiency for the heater plate.

In an embodiment herein, the power source in the humidifier contains a switching power supply to control the current. Specifically, while achieving a power output of up to about 250 W, the voltage to the heating plate is controlled so as to be about 24 V or lower. So as to reduce the chance of electric shock to the user. Without intending to be limited by theory, it is believed that such a shock could occur if the voltage flowing through the heating plate is too large such as, for example, over about 36 V.

Typically the heater plate, the humidifier and/or the medical device would contain a controller which may be, for example, a printed circuit board, a microcontroller, and/or a combination of software and hardware; or a combination of software and hardware. The controller coordinates the various functions, inputs, outputs, etc. of the heater plate, humidifier, and/or medical device. For example, the controller may receive a signal from the switch, a water tank indicator, and/or a water level sensor so as to regulate electricity flowing to the ceramic heating element; i.e., to either allow electricity to flow to the heating element, or to stop such electricity from flowing to the ceramic heating element. The controller may also, for example, receive temperature information from the temperature sensor to determine and regulate the amount of electricity that should flow to the ceramic heating element. The controller may further collect and/or process data received and/or to pass such data on to another unit either via wires, a portable or permanent memory device, a wireless connection, etc.

Turning to the figures, FIG. 1 shows an upside-down, exploded view of an embodiment of a heater plate, 1, of the present invention. The heater plate, 1, containing a thermally-conductive plate, 10, has a top surface, 12, and a bottom surface, 14, opposite the top surface, 12. The bottom surface, 14, contains a temperature sensor, 16, affixed directly to the bottom surface, 14. The bottom surface, 14, also contains a plurality of; or two, thermally-conductive layers, 18, directly-affixed to the bottom surface, 14. A plurality of; or two, ceramic heating elements, 20, are directly-affixed to the plurality of; or two, thermally-conductive layers, 18.

Figure 2:
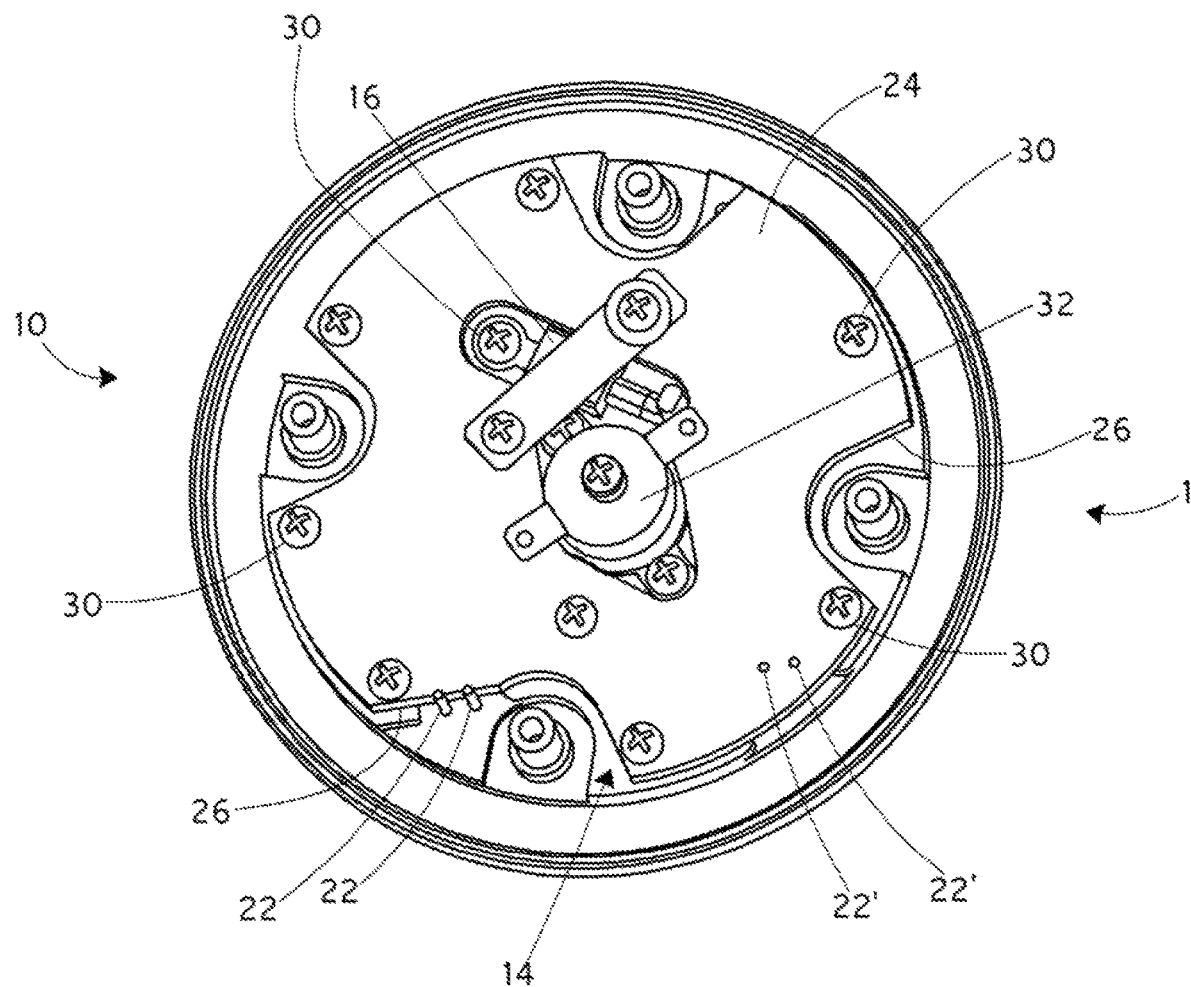
FIG. 2 shows a top view of the bottom surface of an embodiment of the heater plate of the present invention.

In FIG. 1, each ceramic heating element, 20, contains a pair of electrical contacts, 22, which are typically connected (e.g., via electrical wires) either directly or indirectly to the controller (see FIG. 2 at 42). A protective plate, 24, containing a plurality of cutouts, 26, and screw holes, 28, is provided.

When the protective plate, 24, is affixed to the bottom surface, 14, via the screws, 30, and threaded through the screw holes, 28, the protective plate, 24, covers the ceramic heating element, 20, and the thermally conductive layer, 18, to protect them from damage and movement. Furthermore, a switch, 32, in this case, a protection switch, is affixed to the bottom surface, 14. When the temperature sensor, 16, detects that the temperature of the heating plate is too high may send a signal to the controller (see FIG. 2 art 42) to cause the protection switch to stop the current to the ceramic heating element, 20. Alternatively, the switch may be, for example, a pressure-sensitive switch, or other type of switch, as desired.

Typically be a screw (not shown), and protrudes from a cutout, 26, in the protective plate, 24. The wires (not shown) connecting the temperature sensor, 16, to the controller (see FIG. 2 at 42), and/or connecting the electrical contacts, 22, to the controller (see FIG. 2 at 42), may also protrude from the cutouts, 26.

In FIG. 1, the bottom surface, 14, further contains a plurality of slots, 34. Each of the ceramic heating elements, 20, are located in and affixed to a slot, 34, to reduce movement of the ceramic heating element, 20. The slot, 34, may have a plurality of faces, 36, or about three faces, 36. Furthermore, the size and shape of the slot is designed so that the ceramic heating element fits therein snugly; or three sides of the ceramic heating element touch the faces of the slot. Without intending to be limited by theory, it is believed that in such a manner, at least three faces of the ceramic heating element will tough the edges of the slot and therefore touch the bottom surface. This in turn increases the direct transfer of heat form the ceramic heating elements, 20, to the bottom surface, 14, and therefore the thermally-conductive plate, 10, and the heating plate, 1.

FIG. 2 shows a top view of the bottom surface, 14, of an embodiment of the heater plate, 1, of the present invention. The protective plate, 24, is connected to the bottom surface, 14, of the thermally-conductive plate, 10, by a plurality of screws, 30, The electrical contacts, 22, can be seen protruding from the cutout, 26, or through (see 22') the protective plate, 24. The temperature sensor, 16, is directly-attached to the bottom surface, 14, and held in place by a screw, 30. The temperature sensor, 16, is affixed adjacent to the switch, 32, which in this case is a protection switch.

Figure 3:
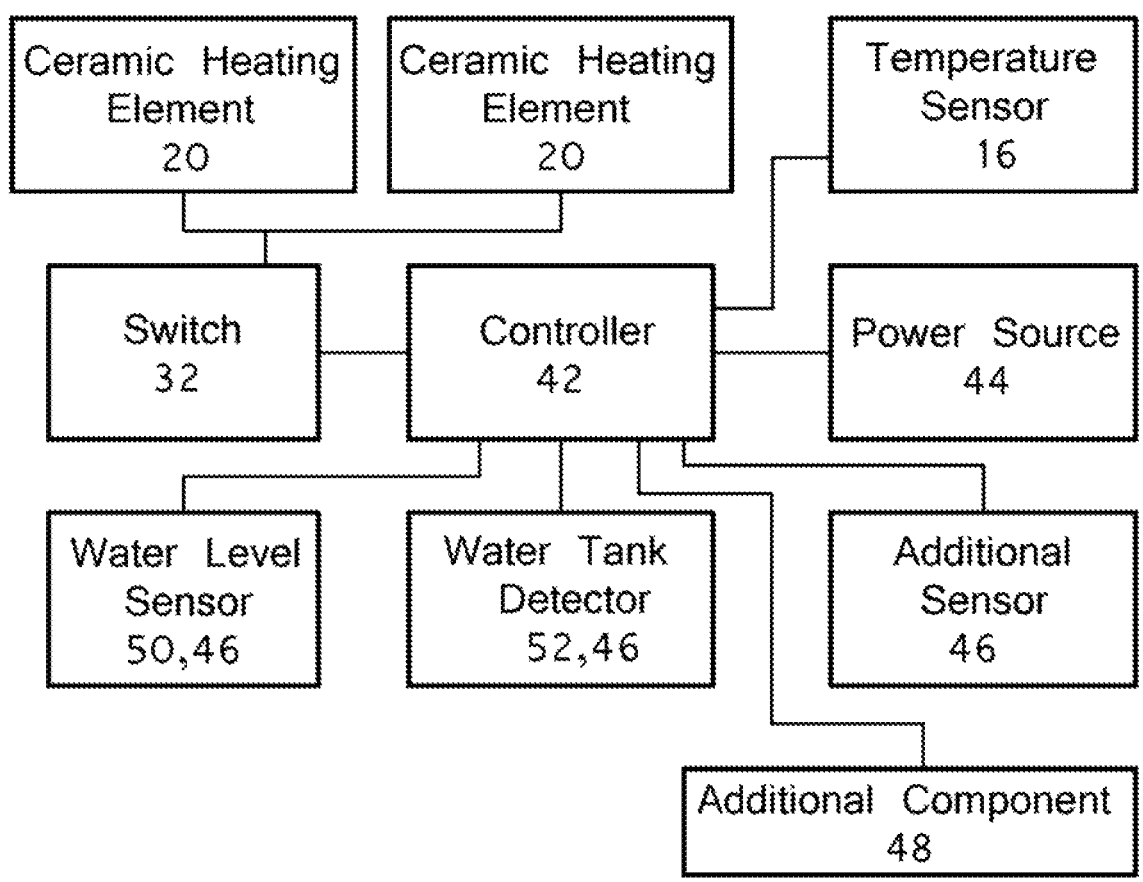
FIG. 3 shows a schematic diagram of an embodiment of the electrical system useful herein.

FIG. 3 shows a schematic diagram of an embodiment of the electrical system, 40, useful herein for a medical device, a humidifier, and/or the thermally-conductive plate. The controller, 42, is electrically- and operatively-connected to a plurality of; or two, ceramic heating elements, 20, via the switch, 32, which may be a pressure-sensitive switch; or a protection switch. The controller, 42, is also electrically- and operatively-connected to a temperature sensor, 16, a power source, 44, an additional sensors, 46, and an additional components, 48, etc.

The additional component useful herein include, for example, a memory or data storage component, a wireless transceiver for data transmission, a wired connection to another device, a clock, etc.

The additional sensor, 46, useful herein include, for example, a water level sensor, 50 (e.g., to detect whether or not sufficient water is present in the water reservoir), a water tank detector, 52 (e.g., to detect whether a water reservoir is present and/or whether or not it is properly attached/affixed), an ambient temperature sensor, a humidity sensor, an air flow sensor, an air speed sensor, a heartbeat sensor, and a combination thereof; or a water level sensor, 50, a water tank detector, 52, an ambient temperature sensor, a humidity sensor, and a combination thereof; or a water level sensor, 50, a water tank detector, 52, an ambient temperature sensor, and a combination thereof.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A heater plate, for a humidifier, the heater plate comprising:
    A) a thermally conductive plate comprising a top surface, and a bottom surface opposite the top surface;
    B) a temperature sensor affixed to the bottom surface;
    C) a thermally conductive layer directly affixed to the bottom surface; and
    D) a plurality of ceramic heating elements directly affixed to the thermally conductive layer,
    wherein the plurality of ceramic heating elements are distributed on the bottom surface of the thermally-conductive plate, and each of the plurality of ceramic heating elements is in a form of strip, and
    wherein the bottom surface of the thermally conductive plate comprises a plurality of slots, and wherein each of the plurality of ceramic heating elements is located in a respective one of the plurality of slots of the thermally conductive plate.

2. The heater plate according to claim 1, wherein the temperature sensor is directly affixed to the bottom surface.

3. The heater plate according to claim 1, wherein the temperature sensor is located between at least two of the ceramic heating elements.

4. The heater plate according to claim 1, further comprising a switch positioned below the bottom surface; or a pressure-sensitive switch; or a protection switch.

5. The heater plate according to claim 4, further comprising a heating circuit comprising a controller, wherein the switch is a protection switch, wherein the controller is operatively connected to the temperature sensor and the protection switch, and wherein the protection switch is operatively connected to the ceramic heating element, and wherein when the temperature sensor detects that the temperature is above a pre-determined point; or 100° C., then the controller signals the protection switch to disconnect the ceramic heating element from the heating circuit.

6. The heater plate according to claim 1, further comprising a protective plate affixed to the bottom surface, wherein the ceramic heating element and the thermally conductive layer are located between the bottom surface and the protective plate.

7. The heater plate according to claim 1, wherein the thermally conductive layer is an adhesive thermally conductive layer; or
    the thermally conductive layer is a thermally conductive silicone sheet, a thermally conductive adhesive, a thermally conductive silicone grease, or a combination of the thermally conductive silicone sheet, the thermally conductive adhesive, and the thermally conductive silicone grease; or
    the thermally conductive layer is a thermally conductive silicone sheet, a thermally conductive adhesive, or a combination of the thermally conductive silicone sheet and the thermally conductive adhesive; or
    the thermally conductive layer is a thermally conductive silicone sheet and a thermally conductive adhesive.

8. The heater plate according to claim 1, further comprising a controller and a power source, wherein the controller is operatively connected to each of the temperature sensor, the ceramic heating element, and the power source.

9. The heater plate according to claim 1, further comprising an additional sensor.

10. A humidifier comprising a heater plate, the heater plate comprising:
    A) a thermally conductive plate comprising a top surface, and a bottom surface opposite the top surface;
    B) a temperature sensor affixed to the bottom surface;
    C) a thermally conductive layer directly affixed to the bottom surface; and
    D) a plurality of ceramic heating elements directly affixed to the thermally conductive layer,
    wherein the plurality of ceramic heating elements are distributed on the bottom surface of the thermally conductive plate, and each of the plurality of ceramic heating elements is in a form of strip, and
    wherein the bottom surface of the thermally conductive plate comprises a plurality of slots, and wherein each of the plurality of ceramic heating elements is located in a respective one of the plurality of slots of the thermally conductive plate.

11. A medical device comprising the heater plate according to claim 1.

12. A medical device comprising the humidifier according to claim 10.

13. The humidifier according to claim 10, wherein the temperature sensor is directly affixed to the bottom surface.

14. The humidifier according to claim 10, wherein the temperature sensor is located between at least two of the ceramic heating elements.

15. The humidifier according to claim 10, wherein the heater plate further comprises a switch positioned below the bottom surface; or a pressure sensitive switch; or a protection switch.

16. The humidifier according to claim 15, wherein the heater plate further comprises a heating circuit comprising a controller, wherein the switch is a protection switch, wherein the controller is operatively connected to the temperature sensor and the protection switch, and wherein the protection switch is operatively-connected to the ceramic heating element, and wherein when the temperature sensor detects that the temperature is above a pre-determined point; or 100° C., then the controller signals the protection switch to disconnect the ceramic heating element from the heating circuit.

17. The humidifier according to claim 10, wherein the heater plate further comprises a protective plate affixed to the bottom surface, wherein the ceramic heating element and the thermally conductive layer are located between the bottom surface and the protective plate.

18. The humidifier according to claim 10, wherein the thermally conductive layer is an adhesive thermally conductive layer; or the thermally conductive layer is a thermally conductive silicone sheet, a thermally conductive adhesive, a thermally conductive silicone grease, or a combination of the thermally conductive silicone sheet, the thermally conductive adhesive and the thermally conductive silicone grease; or the thermally conductive layer is a thermally conductive silicone sheet, a thermally conductive adhesive, or a combination of the thermally conductive silicone sheet and the thermally conductive adhesive; or the thermally conductive layer is a thermally conductive silicone sheet and a thermally conductive adhesive.

\* \* \* \* \*